(12) United States Patent
Tang et al.

(10) Patent No.: US 10,806,430 B2
(45) Date of Patent: Oct. 20, 2020

(54) PROBE TRANSMISSION DEVICE

(71) Applicant: SHENZHEN MINDRAY BIO-MEDICAL ELECTRONICS CO., LTD., Shenzhen (CN)

(72) Inventors: Ming Tang, Shenzhen (CN); Zhenyu Chen, Shenzhen (CN); Leyun Bai, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 710 days.

(21) Appl. No.: 14/975,542

(22) Filed: Dec. 18, 2015

(65) Prior Publication Data
US 2016/0174936 A1   Jun. 23, 2016

Related U.S. Application Data

(63) Continuation of application No. PCT/CN2014/074222, filed on Mar. 27, 2014.

(30) Foreign Application Priority Data

Jun. 19, 2013 (CN) .......................... 2013 1 0244805

(51) Int. Cl.
*A61B 8/00* (2006.01)
*G01S 7/52* (2006.01)
(Continued)

(52) U.S. Cl.
CPC .......... *A61B 8/4466* (2013.01); *A61B 8/4444* (2013.01); *G01S 7/52079* (2013.01);
(Continued)

(58) Field of Classification Search
CPC ....... B66D 1/34; B66B 11/0075; B66B 11/06; B66B 11/08; B66B 11/008;
(Continued)

(56) References Cited

U.S. PATENT DOCUMENTS 1,437,987 A * 12/1922 Miller ...................... B66D 1/34
242/587.1
1,767,938 A * 6/1930 Monnier .................. B66D 1/34
242/388.5
(Continued)

FOREIGN PATENT DOCUMENTS

CN        102087122 A    6/2011

*Primary Examiner* — Katherine L Fernandez
*Assistant Examiner* — Colin T. Sakamoto
(74) *Attorney, Agent, or Firm* — Kory D. Christensen

(57) ABSTRACT

A probe transmission device comprises a drive shaft which is provided with a radial hole and an axial hole, wherein the radial hole is in communication with the axial hole. A rope extends into the axial hole via the radial hole. A fixing component is arranged within the axial hole and fixes the rope within the radial hole. The probe transmission device is provided with the radial hole and the axial hole on the drive shaft. The rope extends into the radial hole and is fixed via the fixing component which is arranged with the axial hole. The structure of the present probe transmission is simple. The surface of the drive shaft does not require a component for fixing the rope, and the surface of the drive shaft is smooth. Interference produced by the rope and components on the surface of the drive shaft is avoided.

17 Claims, 3 Drawing Sheets

(51) Int. Cl.
  *G01S 15/89* (2006.01)
  *A61B 8/12* (2006.01)
(52) U.S. Cl.
  CPC .............. *G01S 15/894* (2013.01); *A61B 8/12* (2013.01); *G01S 15/8993* (2013.01)
(58) Field of Classification Search
  CPC .............. B66B 11/0085; B66B 11/009; B66B 11/0095; A61B 8/4461; A61B 8/4466
  See application file for complete search history.

(56) References Cited

U.S. PATENT DOCUMENTS

| | | | | |
|---|---|---|---|---|
| 1,913,508 A * | 6/1933 | Phillips | .................... | B66D 1/34 242/587.1 |
| 5,167,221 A * | 12/1992 | Chikama | .............. | A61B 1/0052 600/149 |
| 5,901,632 A * | 5/1999 | Ryan | ....................... | D07B 1/025 87/13 |
| 2003/0168551 A1* | 9/2003 | Golden | .................. | B65H 75/28 242/586.1 |
| 2006/0173330 A1 | 8/2006 | Kim | | |
| 2008/0161694 A1 | 7/2008 | Kim | | |
| 2008/0161695 A1* | 7/2008 | Kim | ....................... | A61B 8/483 600/459 |
| 2009/0143682 A1 | 6/2009 | Kadokura | | |
| 2011/0071399 A1* | 3/2011 | Tang | .................... | A61B 8/4455 600/459 |
| 2012/0116233 A1* | 5/2012 | Mah | ...................... | A61B 5/0084 600/476 |

\* cited by examiner

PROBE TRANSMISSION DEVICE

TECHNICAL FIELD

This disclosure relates to medical ultrasonic device field, and more particularly to a probe transmission device.

BACKGROUND

An ultrasound wave probe with three-dimensional imaging function may be named as 3D mechanical probe, which may comprise a transducer unit for transmitting and receiving ultrasound waves. A stepper motor may be used as a drive power source which drives the transducer unit to swing within an angle range under the control of signal. The transducer unit can transmit ultrasound wave and receive ultrasound echo with human tissue information at every angle within the angle range. Thus, the human tissue can be imaged at every angle within the angle range, and a three dimensional image thereof can be constructed. classified as surface 3D mechanical probe and intracavitary 3D 3D mechanical probe can be mechanical probe. The intracavitary 3D mechanical probe may usually use bevel gears, ropes or the like to drive the transducer unit. A rope driving device may comprise a driven shaft, a pulley and a probe transmission device. The probe transmission device may comprise a driving shaft and a rope. The rope may be connected to the driven shaft through the pulley. The transducer unit can be arranged at one end of the driven shaft. When the driving shaft rotates, the driven shaft can be rotated by the rope.

In conventional probe transmission device, a plane can be arranged on the driving shaft and the ends of the ropes can be pressed against the plane by a pressing block fixed with screws. Because the pressing block has a certain volume, when the shaft rotates, the ropes may be interfered by the pressing block, which can lead to a higher probability of error.

SUMMARY

This disclosure provides a probe transmission device which can avoid the interference between the ropes and the pressing block.

A probe transmission device, comprising:

a drive shaft which is provided with an axial hole and a radial hole, wherein the axial hole is in communication with the radial hole;

a rope which extends from the radial hole into the axial hole; and a fixing component which is arranged within the axial hole and fixes the wire rope within the axial hole.

In some embodiments, the drive shaft is equipped with the axial hole and the radial hole, and the wire rope extends from the radial hole into the axial hole, and wire rope is fixed by the fixing component which is provided in the radial hole. The structure of the probe transmission device is simple, and the surface of the drive shaft does not need a component for fixing the rope, and the surface of the drive shaft is smooth. Interference produced by the rope and components on the surface of the drive shaft is avoided.

DETAILED DESCRIPTION

A detailed description of a probe transmission device in accordance with various embodiments of the present disclosure is provided below. While several embodiments are described, it should be understood that this disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

It is noted that when a component is referred as "fixed to" another component, the component can be put directly on another component and also can exists in the center. When a component is referred as "connected to" another component, the component can be put directly on another component and also can exists in the center at the same time. Terms like "perpendicular", "horizontal", "left", "right" and others alike herein are just for the purpose of illustration.

Unless otherwise defined, meanings of all technical and scientific terms herein are the same as common understandings of skill in the art in this technical field of the present disclosure. Terms in detail description of the present disclosure herein are for the purpose of describing specific embodiments, but not for the purpose of confining the present disclosure. Terms like "and/or" herein comprises any and all combination of relating listed embodiments.

Figure 1:
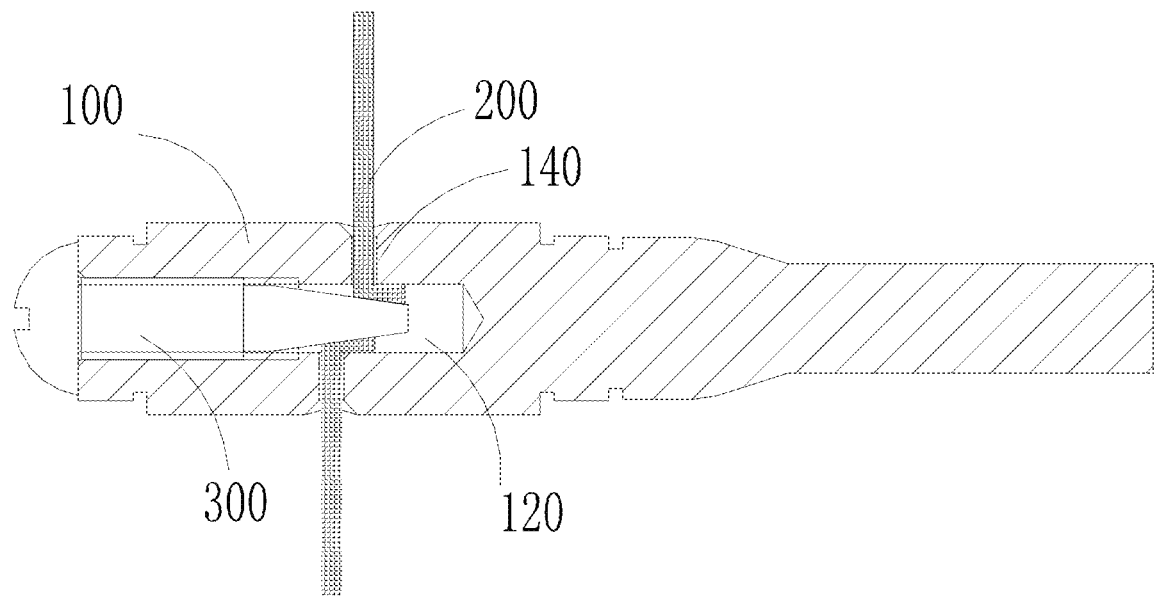
FIG. 1 is a schematic view showing a cross-section of a probe transmission device according to an embodiment of the present disclosure.
Figure 2:
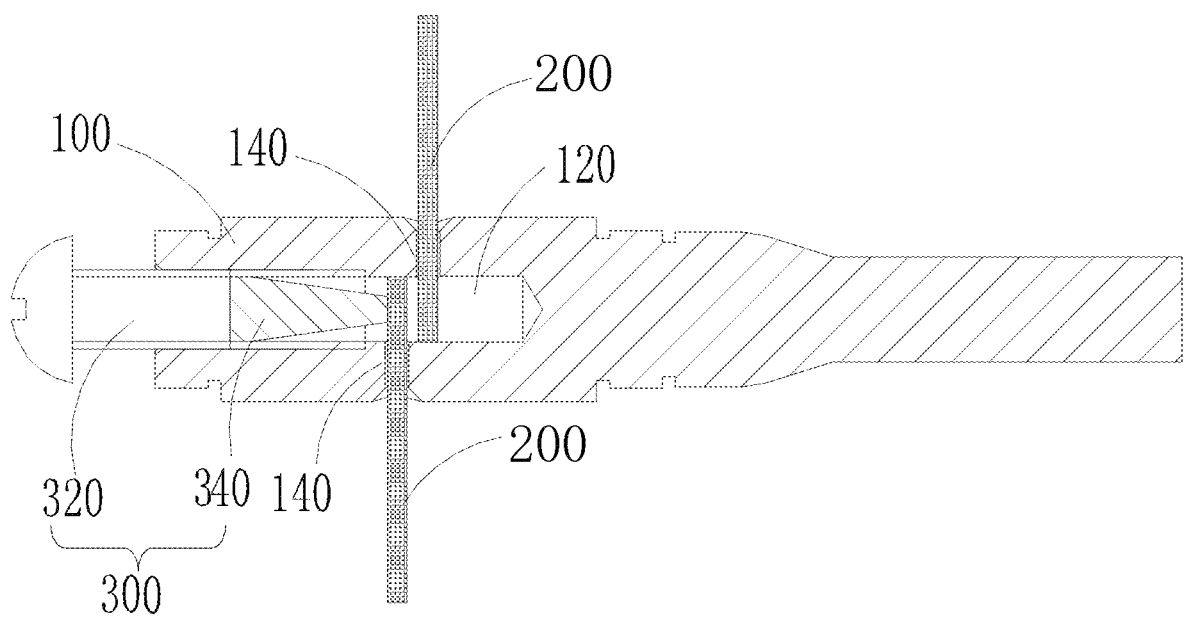
FIG. 2 is a schematic view showing a cross-section of a drive shaft of a probe transmission device according to an embodiment of the present disclosure.

As illustrated in FIG. 1 and FIG. 2, embodiments of this present disclosure provide a probe transmission device. The probe transmission device comprises a drive shaft 100, a pole 300 and a rope 200. The drive shaft is provided with an axial hole 120 and a radial hole 140. The axial hole 120 is in communication with the radial hole 140. The rope 200 extends from the radial hole 140 into the axial hole 120 and be housed in the axial hole 120. The pole 300 is housed within the axial hole 120 and fixes the rope 200 within the axial hole 120. In some embodiments, the pole 300 can be replaced into other fixing parts which are provided in the axial hole 120, such as wax or glue which meets stretch requirement. The fixing parts are injected into the axial hole when in liquid states and fix the rope 200 in the axial hole 120 when the fixing parts are solidified.

In some embodiments, a medial axis of the axial hole 120 is parallel to a medial axis of a drive shaft 100. Due to the medial axis of the axial hole 120 is parallel to the medial axis of the drive shaft 100, pressure of the pole 300 which is housed in the axial hole 120 is even so that service life of the pole 300 can be increased. In some embodiments, the medial axis of the axial hole 120 is parallel to the medial axis of a drive shaft 100, and the pole 300 is set along an extension direction of the axial hole 120 in level state, so the pole 300 is not easy to split away off. In some embodiments, the medial axis of the axial hole 120 is not parallel to the medial axis of the drive shaft 100.

Figure 3:
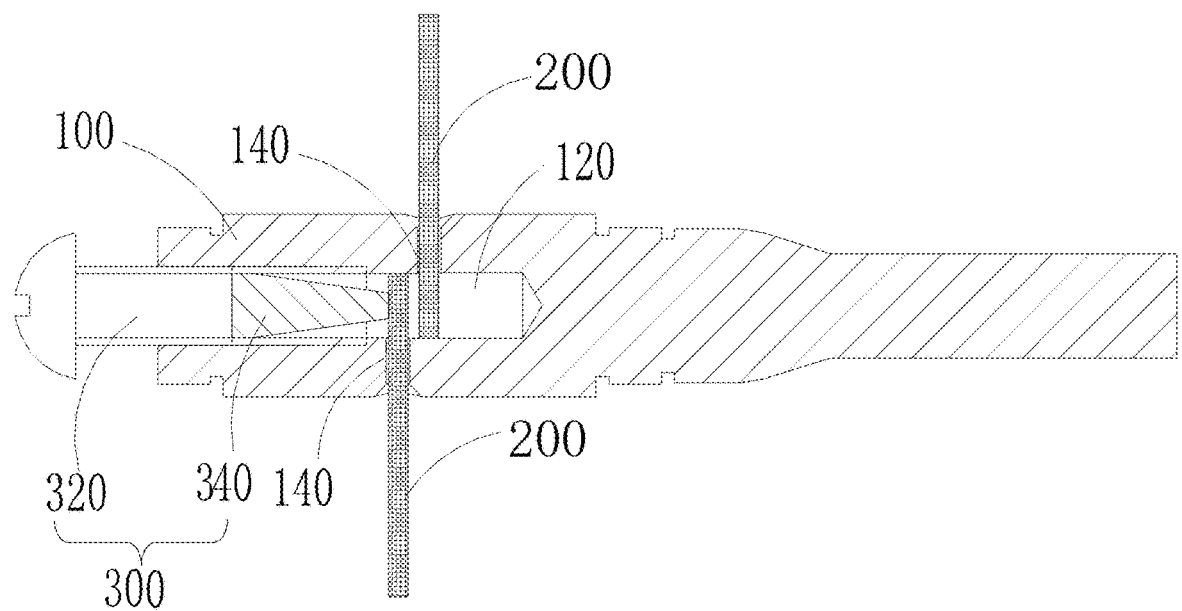
FIG. 3 is a schematic view showing a cross-section of a probe transmission device according to an embodiment of the present disclosure.

As illustrated in FIG. 3, in some embodiments, the axial hole 120 is set in an axis of the drive shaft 100 so that centre of gravity of the drive shaft 100 is distributed evenly and damage caused by driving motor due to uneven gravity distribution is avoided, and the service life of the driving motor and service efficiency are both increased.

In some embodiments, the radial hole 140 is provided in the drive shaft 100 and is in communication with the axial hole 120. In some embodiments, a medial axis of the radial hole 140 is perpendicular to a medial axis of the drive shaft 100, so force direction of the rope 200 is consistent with aperture direction of the axial hole 120. Friction between the rope 200 and hole wall of the radial hole 140 is relatively low, and force of friction is distributed evenly, so the service life of the rope 200 is increased. In other embodiments, the radial hole 140 is provided aslant upon the drive shaft 100, i.e., the medial axis of the radial hole 140 does not need to be provided perpendicular to the medial axis of the drive shaft 100.

In some embodiments, as illustrated in FIG. 3, two radial holes 140 are distributed in different diametric planes of the drive shaft 100, i.e., there exists a distance between the two radial holes 140 along axial direction of the drive shaft 100. When the drive shaft 100 rotates, the rope 200 twines around the drive shaft 100, and there exists no intervention between the rope 200 and the drive shaft 100. In some embodiments, number of the radial hole 140 can be one. When there exists only one radial hole 140, two ends of the rope 200 stretch individually into the radial hole 140 and the rope 200 is fixed within the drive shaft 100 by the fixing component 300. Surface of the drive shaft 100 does not need to provide with components which are used to fix the rope 200, and there exists no intervention between the rope 200 and the drive shaft 100.

Figure 6:
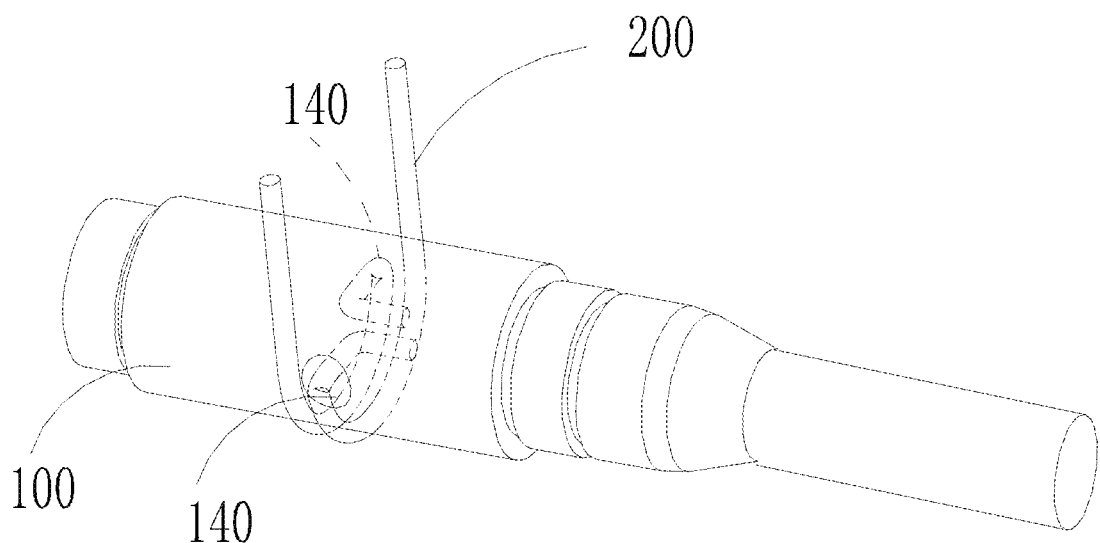
FIG. 6 is a schematic view showing a wire rope twining around a drive shaft according to an embodiment of the present disclosure.

In some embodiments, as illustrated in FIG. 6, the medial axis of the two radial holes 140 and the medial axis of the drive shaft 100 are in the same plane. Two radial holes 140 are distributed in different diametric planes of the drive shaft 100. The diametric plane of the drive shaft 100 is a radial section of the drive shaft 100. When one rope 200 is used for transmitting, two ends of the rope 200 extend individually into the radial hole 140 and fix in the axial hole 120. When two ropes 200 are used for transmitting, two connecting ends of the two ropes 200 and the drive shaft 100 stretches individually into the axial hole 120 and are fixed within the axial hole 120. When the driving shaft 100 rotates, two ropes 200 can twines around the driving shaft 100 along respective diametric planes, and there exists no intervention between the two ropes and any other components on the surface of the drive shaft 100. Angle of rotation is large enough to avoid mistakes. In some embodiments, medial axes of two radial holes 140 are in the same planes, an angle of 180 degrees is formed between the two medial axis. When rotates, the drive shaft 100 can be ensured to liner transfer within rotating angle of ±180 degrees. Force of the drive shaft 100 is distributed evenly, and the drive shaft 100 is relatively steady when rotates. In some embodiments, two medialaxis of the radial holes 140 can be formed in an angle of 90 degrees, 70 degrees and so on.

In some embodiments, the axial hole 120 and the radial hole 140 are counterbores. The radial hole 140 is a counterbore so that a nail head of a screw 320 is embedded in the counterbore and an end of the drive shaft is even. The radial hole 140 is a counterbore so that the radial hole 140 expands and the rope 200 can be stretched into the radial hole 140.

In some embodiments, the pole 300 is arranged within the axial hole 120, and an end of the pole 300 presses against the rope 200 so that the rope 200 fits tightly with the inner wall of the axial hole 120. In some embodiments, two ends of the rope 200 pass though corresponding radial holes 140 individually and be pressed into the axial hole 120. Diameters of the two ropes 200 where the pole 300 presses are slightly larger than a difference between diameters of the axial hole 120 and twice of the rope 200, so the rope 200 can be pressed tightly. In some embodiments, the rope 200 can be pressed at the bottom of the axial hole 120.

Figure 4:
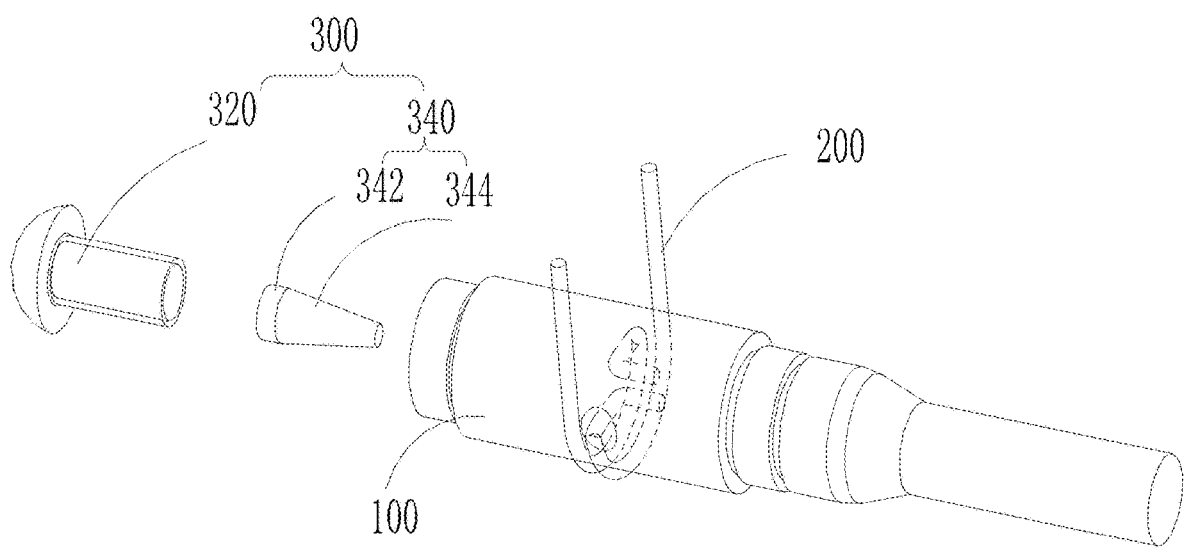
FIG. 4 is a three-dimensional schematic view showing a probe transmission device according to an embodiment of the present disclosure.

In some embodiments, as illustrated in FIG. 4, the pole 300 can comprises a screw 320 and a fixed pin 340. The fixed pin 340 is detachably connected to the screw 320. The rope 200 is fixed to an inner wall of the axial hole 120. During installing, two ends of the rope 200 are pass though the radial hole 140 individually and extend into the axial hole 120, and the fixed pin 340 is provided in the axial hole 120 and the screw 320 is installed to fix the rope 200. The fixed pin 340 is set long enough to get the rope 200 stuck which is most far away from an open end of the axial hole 120. A sum of a diameter of the fixed pin 340 and twice diameters of the rope 200 is larger than a diameter of the axial hole 120, and the rope 200 can be ensured to press tightly against the inner wall of the axial hole 120. The fixed pin 340 is connected detachably with the screw 320. The fixed pins 340 of different lengths are replaced according to a distance between the fixed pin 340 and the axial hole 120. The fixed pins 340 of different diameters are replaced according to the diameter of the axial hole 120 and the diameter of the rope 200.

In some embodiments, an inner wall of the axial hole 120 of the drive shaft 100 is provided with screw threads which match with the screw 320 so that a connection between the screw 320 and the drive shaft 100 is more steady, and a relative displacement between the screw 320 and the axial hole 120 during use which can cause the rope 200 loosened can be prevented. In some embodiments, by turning the screw 320 to rotate, the shift distance of the screw 320 can be controlled accurately s tightness of the rope 200 can be controlled accurately.

In some embodiments, as illustrated in FIG. 4, the screw 320 is a hollow screw. The fixed pin 340 comprises a connection part 342 and a pressing part 344. The connection part 340 of the fixed pin 342 is housed in the hollow screw 320. The pressing part 344 of the fixed pin 340 stretches into the axial hole 120 and fixes the rope 200 to the inner wall of the axial hole 120. During installing and tearing down, the connection part 342 of the fixed pin 340 is easy to be enclosed and be taken out. After the screw 320 is taken out, the fixed pin 340 can be pulled out from the screw 320.

Figure 5:
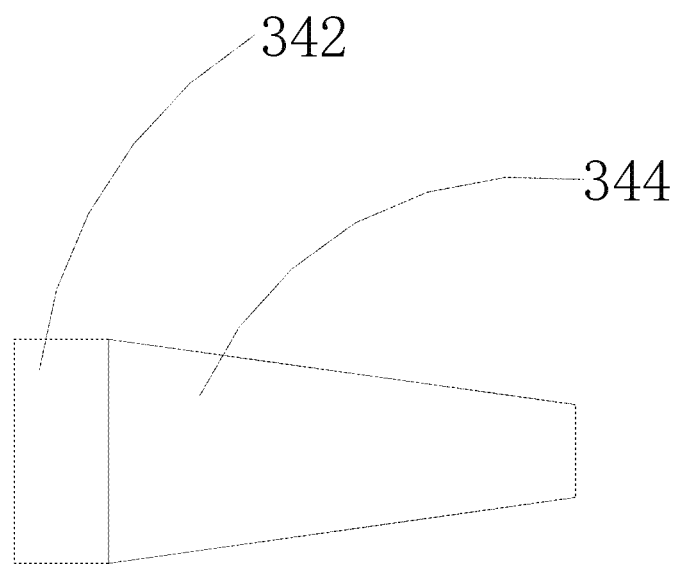
FIG. 5 is a schematic view showing a fixed pin according to an embodiment of the present disclosure.

In some embodiments, as illustrated in FIG. 5, a diameter of the pressing part 344 of the fixed pin 340 which is far away from the connecting part 342 decreases gradually. An interval between the pressing part 344 of the fixed pin 340 and a side wall of the axial hole 120 can be adjusted by adjusting the stretching location of the fixed pin 340 so that the elastic state of the rope 200 can be controlled. Length and a diameter of the pressing part 344 can be calculated by a diameter of the rope 200, a distance between the two ropes and size of the axial hole 120, and enough amount of compression of the two ropes 200 can be ensured.

In some embodiments, the drive shaft 100 of the probe transmission device is provided with the axial hole 120 and the radial hole 140. The rope stretches into the axial hole 120 and be fixed by the pole 300 which is housed in the axial hole 120. Structure of the probe transmission device is simple. Surface of the drive shaft 100 does not need to be provided with components to fix the rope 200. The Surface of the drive shaft 100 is smooth, and intervention between the rope 200 and the surface of the drive shaft 100 is avoided.

The embodiments described above are merely used to illustrate the technical solutions of the present disclosure, but should not be deemed as limitations to the scope of this disclosure. It should be noted that, for those of ordinary skill in the art, without departing from the inventive concept of this disclosure, a number of variations and modifications may be made, while such variations or modifications should be deemed to be included within the scope of this disclosure. Accordingly, the scope of protection of this disclosure should be defined by the appended claims.

The invention claimed is:

1. An ultrasound probe transmission device, comprising:
   a drive shaft comprising an axial hole and two radial holes, wherein the axial hole is in communication with the two radial holes; and a central axis of the axial hole is the same as a rotation axis of the drive shaft;
   two ropes, wherein one of the two ropes extends from one of the two radial holes into the axial hole and the other of the two ropes extends from the other of the two radial holes into the axial hole; and
   a fixing component arranged within the axial hole and configured to press the two ropes against an inner wall of the axial hole.

2. The ultrasound probe transmission device of claim 1, wherein the fixing component is a pole housed within the axial hole.

3. The ultrasound probe transmission device of claim 2, wherein the pole presses the two ropes against the inner wall of the axial hole, and a diameter of a portion of the pole where the pole presses against the two ropes is larger than a difference between a diameter of the axial hole and a diameter of the two ropes.

4. The ultrasound probe transmission device of claim 2, wherein the pole comprises a screw and a pin, wherein the pin is detachably connected with the screw, and the two ropes are fixed to the inner wall of the axial hole by the pin.

5. The ultrasound probe transmission device of claim 4, wherein the inner wall of the axial hole comprises screw threads and the screw is engaged with the screw threads.

6. The ultrasound probe transmission device of claim 4, wherein the screw is a hollow screw, and an end of the pin is housed in the hollow screw.

7. The ultrasound probe transmission device of claim 6, wherein the pin comprises a connection part and a pressing part which is connected with the connection part, the connection part is housed in the hollow screw, and the two ropes are fixed to the inner wall of the axial hole by the pressing part.

8. The ultrasound probe transmission device of claim 7, wherein a diameter of one end of the pressing part of the pin which is away from the connection part decreases gradually.

9. The ultrasound probe transmission device of claim 1, wherein the two radial holes are arranged in the drive shaft at different radial planes of the drive shaft.

10. The ultrasound probe transmission device of claim 9, wherein medial axes of the two radial holes and a medial axis of the drive shaft are located in a same plane.

11. The ultrasound probe transmission device of claim 1, wherein respective medial axes of the two radial holes are perpendicular to a medial axis of the drive shaft.

12. The ultrasound probe transmission device of claim 1, wherein a medial axis of the axial hole is parallel with a medial axis of the drive shaft.

13. The ultrasound probe transmission device of claim 1, wherein the axial hole is provided at a medial axis of the drive shaft.

14. The ultrasound probe transmission device of claim 1, where each of the two radial holes comprises a counterbore.

15. The ultrasound probe transmission device of claim 1, where the axial hole comprises a counterbore.

16. The ultrasound probe transmission device of claim 1, wherein a direction along which the fixing component is inserted in the axial hole to press the two ropes is the same as a direction along which the two ropes extend along the axial hole.

17. The ultrasound probe transmission device of claim 16, wherein the fixing component is tapered.

* * * * *